United States Patent [19]

Slongo et al.

[11] 4,263,505
[45] Apr. 21, 1981

[54] POLYALKYLPIPERIDINE-SPIROOXAZOLONES AND THEIR USE AS LIGHT STABILIZERS

[75] Inventors: Mario Slongo, Muttenz; Erwin Nikles, Liestal, both of Switzerland

[73] Assignee: Ciba-Geigy Corporation, Ardsley, N.Y.

[21] Appl. No.: 132,961

[22] Filed: Mar. 24, 1980

[30] Foreign Application Priority Data

Mar. 27, 1979 [CH] Switzerland ............ 2826/79

[51] Int. Cl.$^3$ .............. C07D 413/04; C08K 5/35
[52] U.S. Cl. ............ 260/45.8 NZ; 260/45.9 NP; 546/19
[58] Field of Search ........... 546/19; 260/48.5 NZ, 260/48.5 NP

[56] References Cited

U.S. PATENT DOCUMENTS 4,107,139 8/1978 Mayer et al. ............ 260/45.8 NZ
4,110,334 8/1978 Mayer et al. ............ 546/19

FOREIGN PATENT DOCUMENTS 8,084 2/1980 European Pat. Off. ......... 260/45.8 NZ
8,102 2/1980 European Pat. Off. ......... 260/45.8 NZ
2,500,314 7/1975 Fed. Rep. of Germany ... 260/45.8 NZ Primary Examiner—Henry R. Jiles Assistant Examiner—Robert T. Bond
Attorney, Agent, or Firm—Harry Falber

[57] ABSTRACT

Compounds of the formula

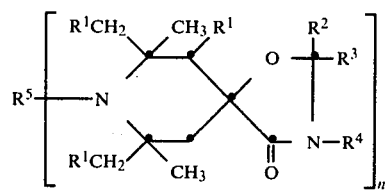

and their acid addition salts, wherein n is an integer from 1 to 4, $R^1$ is hydrogen or $CH_3$, each of $R^2$ and $R^3$ independently is hydrogen, $C_1-C_{18}$alkyl, $C_6-C_{10}$aryl or $C_7-C_9$aralkyl which is unsubsititued or substituted by chlorine or $C_1-C_4$alkyl, or $R^2$ and $R^3$ together with the carbon atom to which they are attached form a cycloalkane or alkylcycloalkane radical containing 5 to 20 carbon atoms or a polyalkylpiperidine radical, $R^4$ is a monovalent radical as defined in claim 1, and $R^5$ is a mono- to tetravalent radical as defined in claim 1. These compounds are valuable stabilizers for plastics. They are obtained by N-substitution of the compounds in which $R^4$ and $R^5$ are hydrogen.

11 Claims, No Drawings

POLYALKYLPIPERIDINE-SPIROOXAZOLONES AND THEIR USE AS LIGHT STABILIZERS

It is known that polyalkylpiperidines which are substituted in the 4-position are valuable light stabilisers for organic materials, especially for plastics. Thus polyalkylpiperidine-4-spirooxazolones in which the nitrogen atom is substituted by hydrogen, oxygen, hydroxyl or lower alkyl, have been disclosed as light stabilisers in German Offenlegungsschrift No. 2 606 026.

These known polyalkylpiperidine derivatives are excellent light stabilisers for plastics. For certain end uses, however, the volatility and tendency to migration of these known compounds is too high. This is particularly the case when the plastics are used in thin layers, for example in fibres, films or coatings. Moreover, many of the known spiro compounds are sparingly soluble in polymers and this results in inadequate compatibility in certain plastics. It has now been found that specific polyalkylpiperidine-4-spirooxazolones possess a substantially lower volatility and lesser tendency to migration than the known polyalkylpiperidine-4-spirooxazolones and also have better compatibility with certain plastics.

Accordingly, the invention provides compounds of the formula I

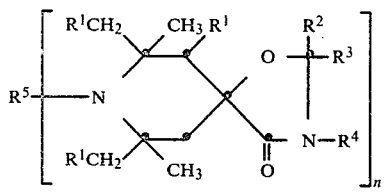

and their acid addition salts, wherein n is an integer from 1 to 4, $R^1$ is hydrogen or $CH_3$, each of $R^2$ and $R^3$ independently is hydrogen, $C_1$–$C_{18}$alkyl, $C_6$–$C_{10}$aryl or $C_7$–$C_9$aralkyl which is unsubstituted or substituted by chlorine or $C_1$–$C_4$alkyl, or $R^2$ and $R^3$ together with the carbon atom to which they are attached form a cycloalkane or alkylcycloalkane radical containing 5 to 20 carbon atoms or a polyalkylpiperidine radical, $R^4$ is hydrogen, $C_1$–$C_8$alkyl, allyl, propargyl, glycidyl or $C_7$–$C_9$aralkyl which is unsubstituted or substituted by $C_1$–$C_4$alkyl, and $R^5$, if n is 1, is hydrogen, $C_1$–$C_8$alkyl, $C_3$–$C_8$alkenyl, $C_3$–$C_5$alkynyl, $C_7$–$C_9$aralkyl which is unsubstituted or substituted by $C_1$–$C_4$alkyl, or is a radical —$CH_2$—$CH(R^6)$—$OR^7$, wherein $R^6$ is hydrogen, $CH_3$, $C_2H_5$ or phenyl, and $R^7$ is hydrogen or the acyl radical of an aliphatic, cycloaliphatic or aromatic monocarboxylic acid containing not more than 18 carbon atoms, and, if n is 2, $R^5$ is 1,4-buten-2-ylene, m- or p-xylylene or a radical of the formula

—$CH_2$—$CH(R^6)$—O—$R^8$—O—$CH(R^6)$—$CH_2$— wherein $R^6$ is as defined above and $R^8$ is the diacyl radical of an aliphatic, cycloaliphatic or aromatic dicarboxylic acid containing 3 to 14 carbon atoms, and, if n is 3, $R^5$ is a radical of the formula

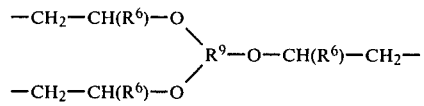

wherein $R^6$ is as defined above and $R^9$ is the triacyl radical of an aliphatic or aromatic tricarboxylic acid containing 4 to 18 carbon atoms, and, if n is 4, $R^5$ is a radical of the formula

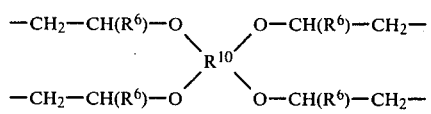

wherein $R^6$ is as defined above and $R^{10}$ is the tetraacyl radical of an aliphatic or aromatic tetracarboxylic acid containing 6 to 20 carbon atoms, with the proviso that, if $R^5$ is hydrogen or $C_1$–$C_4$alkyl, $R^4$ cannot be hydrogen.

$R^2$ and $R^3$ as a alkyl can be unbranched or branched alkyl, e.g. methyl, ethyl, propyl, isobutyl, hexyl, 2-ethylhexyl, isooctyl, decyl, dodecyl or octadecyl. $R^2$ and $R^3$ as unsubstituted or substituted aryl can be e.g. phenyl, naphthyl, chlorophenyl, tolyl or 4-butylphenyl. $R^2$ and $R^3$ as aralkyl can be e.g. benzyl, phenylethyl or phenylpropyl.

A cycloalkane or alkylcycloalkane radical formed by $R^2$ and $R^3$ together with the carbon atom to which they are attached can be e.g. a cyclopentane, cyclohexane, methylcyclohexane, cyclodecane, cyclooctane, cyclododecane or dimethylcyclododecane radical.

It is preferred that each of $R^2$ and $R^3$ independently is alkyl of 1 to 12 carbon atoms or phenyl, or $R^2$ and $R^3$ together with the carbon atom to which they are attached form a $C_6$–$C_{12}$cycloalkane radical.

$R^4$ and $R^5$ as alkyl can be e.g. methyl, propyl, butyl, hexyl, 2-ethylhexyl or n-octyl.

$R^5$ as alkenyl can be e.g. allyl, methallyl, butenyl, hexenyl or octenyl. $R^4$ and $R^5$ as aralkyl can be e.g. benzyl, phenylethyl or 4-methylbenzyl.

A carboxylic acid radical $R^7$ can be e.g. the radical of acetic acid, acrylic acid, propionic acid, butyric acid, caprylic acid, palmitic acid, oleic acid, stearic acid, benzoic acid, phenylacetic acid or naphthoic acid. A dicarboxylic acid radical $R^8$ can be e.g. the divalent radical of malonic acid, succinic acid, maleic acid, adipic acid, itaconic acid, sebacic acid, suberic acid, phthalic acid, terephthalic acid, isophthalic acid or 4,4'-diphenyl-, bicyclo[2.2.1]heptene- or bicyclo[2.2.1]heptane-2,3-dicarboxylic acid.

A tricarboxylic acid radical $R^9$ can be e.g. the trivalent radical of tricarballylic acid, nitrilotriacetic acid, aconitic acid or trimellitic acid. A tetracarboxylic acid radical $R^{10}$ can be e.g. the tetravalent radical of methylenedimalonic acid, methylenediphthalic acid or pyromellitic acid.

Preferred compounds are those of the formula I in which $R^1$ is hydrogen, and those wherein n is 1 or 2.

Further preferred compounds of the formula I are those in which n is 1 and $R^4$ is hydrogen and $R^5$ is allyl, benzyl, 2-hydroxyethyl or 2-hydroxypropyl, as well as compounds of the formula I in which n is 1 and $R^4$ is allyl or benzyl and $R^5$ is hydrogen.

The present invention also comprises the salts of compounds of the formula I which are formed by addition of acids in amounts which are at most equivalent to the piperidine groups. Such acids can be inorganic acids, for example sulfuric acid, hydrochloric acid or phosphoric acid, organic carboxylic acids, such as formic acid, acetic acid, oxalic acid, maleic acid, benzoic acid or salicylic acid, organic sulfonic acids, such as methanesulfonic acid or p-toluenesulfonic acid, or organic phosphorus-containing acids, such as diphenylphosphoric acid, methanephosphonic acid or diphenylphosphinic acid.

Examples of compounds of the formula I are: 8-allyl-7,7,9,9-tetramethyl-2,2-dimethyl-1-oxa-3,8-diaza-4-oxo-spiro[4.5]decane, 8-benzyl-7,7,9,9-tetramethyl-2,2-dimethyl-1-oxa-3,8-diaza-4-oxa-spiro[4.5]decane, 8-(2-hydroxyethyl)-7,7,9,9-tetramethyl-2-methyl-2-ethyl-1-oxa-3,8-diaza-4-oxo-spiro[4.5]decane, 8-(2-acetoxyethyl)-7,7,9,9-tetramethyl-2-methyl-2-ethyl-1-oxa-3,8-diaza-4-oxo-spiro[4.5]decane, 8-(2-benzoyloxyethyl)-7,7,9,9-tetramethyl-2-methyl-2-phenyl-1-oxa-3,8-diaza-4-oxo-spiro[4.5]decane, 8-(2-phenylethyl)-7,7,9,9-tetramethyl-2-phenyl-1-oxa-3,8-diaza-4-oxo-spiro[4.5]decane, 8-(2-phenyl-2-hydroxyethyl)-7,7,9,9-tetramethyl-2,2-dibutyl-1-oxa-3,8-diaza-4-oxo-spiro[4.5]decane, 8-(2-stearoyloxyethyl)-6,7,9-trimethyl-7,9-diethyl-2-methyl-2-benzyl-1-oxa-3,8-diaza-4-oxo-spiro[4.5]decane, 1,4-bis-(7,7,9,9-tetramethyl-2,2-diethyl-1-oxa-3,8-diaza-4-oxo-spiro[4.5]-dec-8-yl)-but-2-ene, α,α'-bis-(7,7,9,9-tetramethyl-2-propyl-1-oxa-3,8-diaza-4-oxo-spiro[4.5]dec-8-yl)-m-xylylene, di-[2-(7,7,9,9-tetramethyl-2,2-dibutyl-1-oxa-3,8-diaza-4-oxo-spiro[4.5]dec-8-yl)-ethyl] succinate, di-[2-(7,7,9,9-tetramethyl-2,2-dibutyl-1-oxa-3,8-diaza-4-oxo-spiro[4.5]dec-8-yl)-propyl] adipate, di-[2-(7,7,9,9-tetramethyl-2,2-dibutyl-1-oxa-3,8-diaza-4-oxo-spiro[4.5]-dec-8-yl)-ethyl] isophthalate, tri-[2-(7,7,9,9-tetramethyl-2,2-dibutyl-1-oxa-3,8-diaza-4-oxo-spiro[4.5]dec-8-yl)-ethyl] trimellitate, tetra-[2-(7,7,9,9-tetramethyl-2,2-dibutyl-1-oxa-3,8-diaza-4-oxo-spiro[4.5]dec-8-yl)-ethyl] pyromellitate, 3-allyl-2,2,4,4-tetramethyl-7-oxa-3,14-diaza-15-oxo-dispiro[5.1.5.2-]pentadecane, di-[2-(2,2,4,4-tetramethyl-7-oxa-3,14-diaza-15-oxo-dispiro-[5.1.5.2]pentadec-3-yl)-ethyl] sebacate, 3-benzyl-2,2,4,4-tetramethyl-7-oxa-3,20-diaza-21-oxo-dispiro-[5.1.11.2]-heneicosane and 1,4-di-(2,2,4,4-tetramethyl-7-oxa-3,20-diaza-21-oxo-dispiro[5.1.11.2-]heneicos-3-yl)-but-2-ene, 1,4-di-(2,2,4,4-tetramethyl-7-oxa-3,20-diaza-21-oxo-dispiro[5,1,11,2]-heneicosyl-3)-butene-2, 2,2,4,4-tetramethyl-7-oxa-3-aza-20-(methyl)aza-21-oxo-dispiro-[5,1,11,2]-heneicosane, 2,2,4,4-tetramethyl-7-oxa-3-aza-20-(benzyl)aza-21-oxo-dispiro-[5,1,11,2]-heneicosane, 2,2,4,4-tetramethyl-7-oxa-3-aza-20-(2-propenyl)aza-21-oxo-dispiro-[5,1,11,2]-heneicosane, 2,2,4,4-tetramethyl-7-oxa-3-aza-20-(butyl)aza-21-oxo-dispiro-[5,1,11,2]-heneicosane, 2,2,4,4-tetramethyl-7-oxa-3-aza-20-(glycidyl)aza-21-oxo-dispiro-[5,1,11,2]-heneicosane.

The compounds of the formula I, wherein $R^4$ and $R^5$ are hydrogen, are known from German Offenlegungsschrift No. 2 606 026. The compounds of the formula I are obtained from these compounds by introducing the substituent $R^4$ at the oxazolone-nitrogen or by introducing the substituent $R^5$ at the piperidine-nitrogen, or by the stepwise introduction of both substituents.

The introduction of $R^4$ is preferably accomplished by converting the NH compound by reaction with strong alkali bases to the corresponding alkali compounds, which are then reacted with alkyl, allyl, propargyl, glycidyl or aralkyl halides. Conversion into the alkali compounds is preferably carried out by the phase transfer method using a solvent in which the alkali bases are not soluble, so that these are present as solid phase. Examples of suitable alkali bases are alkali oxides, amides, hydrides and alkoxides. However, it is preferred to use alkali hydroxides, such as potassium hydroxide. Examples of suitable solvents are diethyl ether, tetrahydrofurane, dioxan, benzene or toluene. The subsequent reaction with a halogen compound results in the formation of an alkali halide, which is likewise insoluble in these solvents and can therefore be simply removed by filtration. Examples of suitable halogen compounds are methyl iodide, butyl bromide, allyl chloride, benzyl chloride or xylylene dibromide.

The introduction of $R^5$ is effected by direct reaction with the NH compound with the substitution reagents. Suitable substitution reagents. Suitable substitution reagents are again the halides such as alkyl, alkenyl, alkynyl or aralkyl halides. It is also possible to add weak bases to the reaction mixture, e.g. alkali metal carbonates or alkaline earth metal oxides, which bind the hydrogen halide which is formed. Compounds of the formula I, wherein $R^5$ is a hydroxyalkyl or hydroxyaralkyl radical can be obtained by reaction of the NH compounds with the corresponding alkylene oxides or with styrene oxide. These hydroxyl compounds can be esterified with mono-, di-, tri- or tetracarboxylic acids to produce the corresponding N-acyloxyalkyl or N-acyloxyaralkyl compounds.

If it is desired to introduce substituents both at the oxazolone nitrogen and at the piperidine-nitrogen, then it is advantageous to introduce $R^4$ first and then $R^5$ by the methods described above.

Especial importance attaches to the stabilisation of polyolefins, styrene polymers and polyurethanes, for which the compounds of the formula I are most suitable.

Examples of such plastics are high density and low density polyethylene, polypropylene, ethylene/propylene copolymers, polystyrene, styrene/butadiene/acrylonitrile copolymers, mixtures of polyolefins or of styrene polymers and polyurethanes based on polyethers or polyesters, in the form of lacquers, elastomers or foams.

The stabilisers are added to the plastics in a concentration of 0.01 to 5% by weight, based on the material to be stabilised. Preferably, 0.1 to 1% by weight of the compounds, based on the material to be stabilised, is incorporated into the latter.

Incorporation can be effected, for example, by blending in at least one of the light stabilisers of the invention and, if desired, further additives, by methods conventionally employed in the art, before or during shaping, or by applying the dissolved or dispersed compounds to the polymer, with subsequent evaporation of the solvent if necessary.

In addition to the compounds of the formula I, still further known stabilisers can also be added to the plastics. These stabilisers can be e.g. antioxidants, light stabilisers or metal deactivators, or also costabilisers, for example those of the organic phosphite type. Furthermore, other additives customary in plastics technology, for example flame retardants, antistatic agents, plasticisers, lubricants, blowing agents, pigments, reinforcing materials or fillers, can also be added.

When known stabilisers are used concurrently, synergistic effects can be obtained. This frequently happens especially when other light stabilisers or organic phosphites are used concurrently. The concurrent use of antioxidants when stabilising polyolefins is of particular importance.

The invention therefore also relates to the plastics stabilised by the addition of 0.1 to 5% by weight of a compound of the formula I, which plastics, if desired, can also contain other known and customary additives. The stabilised plastics can be used in very diverse forms, for example as films, fibres, ribbons or profiles or as binders for lacquers, adhesives or putties.

The manufacture and use of the compounds of the invention is described in more detail in the following Examples. Parts and percentages are by weight.

EXAMPLES 1–3: Substitution at the piperidine-nitrogen 18.2 (0.05 mole) of 2,2,4,4-tetramethyl-7-oxa-3,20-diaza-21-oxo-dispiro[5.1.11.2]-heneicosane are dissolved in 100 ml of dioxan. 1 g of potassium iodide, 7.3 g (0.06 mole) of allyl bromide, and 9.7 g of $K_2CO_3$ are added to the solution and the mixture is heated to reflux. After a reaction time of 30 hours, the reaction mixture is filtered hot. The title compound crystallises out from the filtrate on cooling and is recrystallised from ligroin.

Melting point 223°–26° C.
Elemental analysis:
calculated: C=74.2%; H=10.96%; N=6.92%;
found: C=74.0%; H=11.1%; N=7.0%.

The procedure described above is repeated, using an equimolar amount of benzyl chloride in place of allyl bromide. 3-Benzyl-2,2,4,4-tetramethyl-7-oxa-3,20-diaza-21-oxo-dispiro[5.1.11.2]heneicosane is obtained.

Melting point 152°–154°.
Elemental analysis:
calculated: C=76.60%; H=10.20%; N=6.16%;
found: C=76.83%; H=10.13%; N=6.32%.

The same amount (0.05 mole) of 2,2,4,4-tetramethyl-7-oxa-3,20-diaza-21-oxo-dispiro[5.1.11.2]heneicosane is dissolved in 50 ml of methanol and the solution is allowed to react for 30 hours with 0.06 mole of ethylene oxide in an autoclave at 120° C. 3-Hydroxyethyl-2,2,4,4-tetramethyl-7-oxa-3,20-diaza-21-oxo-dispiro[5.1.11.2-]heneicosane is obtained in the form of white crystals. Melting point 260°–262° C. (recrystallisation from isopropanol).

Elemental analysis: ($C_{24}H_{44}N_2O_3$)
calculated: C=70.55%; H=10.85%; N=6.85%;
found: C=70.36%; H=10.68%; N=6.93%.

EXAMPLES 4–6: Substitution at the oxazolone-nitrogen 18.2 g (0.05 mole) of 2,2,4,4-tetramethyl-7-oxa-3,20-diaza-21-oxo-dispiro[5.1.11.2]-heneicosane are dissolved in 200 ml of abs. tetrahydrofurane and 3.5 g (10.06 moles) of tetrabutylammonium chloride power are added to the solution. The mixture is heated to 60°–70° C., then a solution of 6 g (0.05 mole) of allyl bromide in 20 ml of abs. tetrahydrofurane is slowly added dropwise. When this addition is complete, the reaction mixture is stirred at the same temperature for 3 hours, then cooled and filtered. The filtrate is concentrated and the residue is recrystallised from acetonitrile. The resultant 2,2,4,4-tetramethyl-7-oxa-3,20-diaza-20-allyl-21-oxo-dispiro[5.1.11.2]-heneicosane is a white crystalline substance which melts at 120°–121° C.

Analysis:
calculated: C=74.21%; H=10.96%; N=6.92%;
found: C=74.51%; H=10.95%; N=6.94%.

The above procedure is repeated using an equimolar amount of benzyl chloride instead of allyl bromide. The product is 2,2,4,4-tetramethyl-7-oxa-3,20-diaza-20-benzyl-21-oxo-dispiro[5.1.11.2]-heneicosane with a melting point of 150°–151° C. (recrystallisation from acetonitrile).

Elemental analysis:
calculated: C=76.60%; H=10.20%; N=6.16%;
found: C=76.59%; H=10.18%; N=6.38%.

EXAMPLE 7: Stabilisation of propylene against light 100 parts of polypropylene powder (Moplen, fibre grade, manufactured by Montedison), 0.2 part of β-(3,5-di-tert-butyl-4-hydroxyphenyl)-propionic acid octadecyl ester and 0.25 part of a stabiliser of Table 1 are homogenised in a Brabender plastograph for 10 minutes at 200° C. The resultant plastic mass is removed from the kneader as quickly as possible and pressed to a 2–3 mm sheet in a toggle press. A portion of the sheet is cut out and pressed between two ultra-gloss rigid aluminium sheets with a hand-operated hydraulic laboratory press for 6 minutes at 260° C. to a 0.1 mm sheet, which is immediately chilled in cold water. Segments are then punched out of this sheet and exposed in the xenotest 1200. These samples are taken out of the exposure apparatus at regular intervals and examined for their carbonyl content in a IR spectrophotometer. The increase in the carbonyl extinction at 5.85μ during exposure is a reference value for the degradation of the polymer by photooxidation [see L. Balaban et al., J. Polymer Sci., Part C; 22, 1059–1071 (1969)] and, as experience shows, is associated with a decrease in the mechanical properties of the polymer. The time taken till a carbonyl extinction of about 0.3 is reached, at which value the comparison sheet is brittle, serves as an indication of the protective action. The compounds of the present invention have not reached this carbonyl extinction after 5100 hours.

The protective action of the stabilisers of the invention is illustrated in Table 1.

TABLE 1

Stabilisation of polypropylene with compounds of the formula

| R = | exposure time | carbonyl extinction |
|---|---|---|
| benzyl | 5100 h | 0.17 |
| allyl | 5100 h | 0.25 |
| without stabiliser | 800 h | 0.30 |

What is claimed is:
1. A compound of the formula

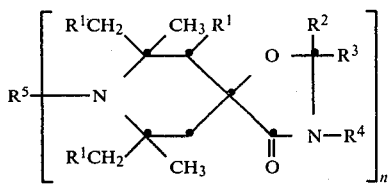

and their acid addition salts, wherein n is an integer from 1 to 4, $R^1$ is hydrogen or $CH_3$, each of $R^2$ and $R^3$ independently is hydrogen, $C_1$-$C_{18}$alkyl, $C_6$-$C_{10}$aryl or $C_7$-$C_9$aralkyl which is unsubstituted or substituted by chlorine or $C_1$-$C_4$alkyl, or $R^2$ and $R^3$ together with the carbon atom to which they are attached form a cycloalkane or alkylcycloalkane radical containing 5 to 20 carbon atoms or a polyalkylpiperidine radical, $R^4$ is hydrogen, $C_1$-$C_8$alkyl, allyl, propargyl, glycidyl or $C_7$-$C_9$aralkyl which is unsubstituted or substituted by $C_1$-$C_4$alkyl, and $R^5$, if n is 1, is hydrogen, $C_1$-$C_8$alkyl, $C_3$-$C_8$alkenyl, $C_3$-$C_5$alkynyl, $C_7$-$C_9$aralkyl which is unsubstituted or substituted by $C_1$-$C_4$alkyl, or is a radical —$CH_2$—$CH(R^6)$—$OR^7$, wherein $R^6$ is hydrogen, $CH_3$, $C_2H_5$ or phenyl, and $R^7$ is hydrogen or the acyl radical of an aliphatic, cycloaliphatic or aromatic monocarboxylic acid containing not more than 18 carbon atoms, and, if n is 2, $R^5$ is 1,4-buten-2-ylene, m- or p-xylylene or a radical of the formula

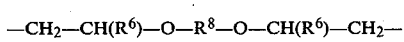

wherein $R^6$ is as defined above and $R^8$ is the diacyl radical of an aliphatic, cycloaliphatic or aromatic dicarboxylic acid containing 3 to 14 carbon atoms, and, if n is 3, $R^5$ is a radical of the formula

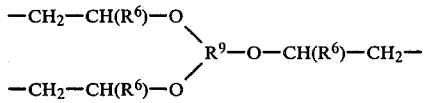

wherein $R^6$ is as defined above and $R^9$ is the triacyl radical of an aliphatic or aromatic tricarboxylic acid containing 4 to 18 carbon atoms, and, if n is 4, $R^5$ is a radical of the formula

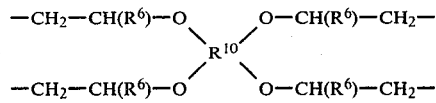

wherein $R^6$ is as defined above and $R^{10}$ is the tetraacyl radical of an aliphatic or aromatic tetracarboxylic acid containing 6 to 20 carbon atoms, with the proviso that, if $R^5$ is hydrogen or $C_1$-$C_4$alkyl, $R^4$ cannot be hydrogen.

2. A compound according to claim 1 of formula I, wherein $R^1$ is hydrogen.

3. A compound according to claim 1 of formula I, wherein n is 1 or 2.

4. A compound according to claim 1 of formula I, wherein each of $R^2$ and $R^3$ independently is $C_1$-$C_{12}$alkyl or phenyl, or $R^2$ and $R^3$ together with the carbon atom to which they are attached form a $C_6$-$C_{12}$cycloalkane ring.

5. A compound according to claim 1 of formula I, wherein n is 1, $R^4$ is hydrogen, and $R^5$ is allyl, benzyl, 2-hydroxyethyl or 2-hydroxypropyl.

6. A compound according to claim 1 of formula I, wherein n is 1, $R^4$ is allyl or benzyl and $R^5$ is hydrogen.

7. A method of stabilizing plastics which comprises incorporating therein an effective stabilizing amount of a compound according to claim 1.

8. A method according to claim 7, wherein the plastics to be stabilised are polyolefins, styrene polymers or polyurethanes.

9. A method according to claim 7, wherein the compound of the formula I is used in an amount of 0.01 to 0.5% by weight, based on the plastics material to be stabilised.

10. A stabilised plastics material containing 0.01 to 5% by weight of at least one compound of the formula I as claimed in claim 1.

11. A stabilised plastics material according to claim 10 which contains other known and conventional additives.

* * * * *